(12) United States Patent
Hemmerlin

(10) Patent No.: US 7,540,201 B1
(45) Date of Patent: Jun. 2, 2009

(54) CROSSHEAD DESIGN FOR UNIVERSAL TESTING MACHINE

(75) Inventor: John Hemmerlin, Grove City, PA (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 11/983,702

(22) Filed: Nov. 9, 2007

(51) Int. Cl.
*G01N 3/02* (2006.01)
*G01N 3/04* (2006.01)
(52) U.S. Cl. ......................................... 73/856; 73/860
(58) Field of Classification Search ............ 73/760–860
See application file for complete search history.

(56) References Cited

U.S. PATENT DOCUMENTS

| | | | | |
|---|---|---|---|---|
| 1,885,855 A | * | 11/1932 | Moran | 73/859 |
| 3,403,549 A | * | 10/1968 | Griffin | 73/859 |
| 5,092,179 A | * | 3/1992 | Ferguson | 73/790 |
| 7,051,600 B1 | * | 5/2006 | Cavallaro et al. | 73/862.041 |

* cited by examiner

*Primary Examiner*—Harshad Patel
*Assistant Examiner*—Punam Patel
(74) *Attorney, Agent, or Firm*—Day Pitney LLP

(57) ABSTRACT

The crosshead for a universal testing machine includes a interior face which is formed at angle to the front face which is typically about 17°. A wedge pocket is machined with walls perpendicular to the interior face, and therefore at an angle other than perpendicular to the front surface of the crosshead. This allows a rectangular steel plate to be oriented to match the machine column locations. Therefore, the material cost is significantly reduced as no special casting shape is required.

15 Claims, 5 Drawing Sheets

CROSSHEAD DESIGN FOR UNIVERSAL TESTING MACHINE

BACKGROUND OF THE INVENTION

1. Field of the Invention

The present invention relates to a rectangular crosshead design for a universal testing machine wherein the specimen pocket is machined at an angle to the front surface of the crosshead rather than perpendicular to the front surface.

2. Description of the Prior Art

In the prior art, the universal testing machine for determining tensile strength and similar characteristics of a sample is well developed. The testing samples in universal testing machines are typically held by jaws which are mounted in wedge-shaped pockets formed in crossheads. These wedge-shaped pockets of the crosshead and the jaws contained therein are configured and arranged to exert a holding force on the specimen. These pockets are typically machined with sides that are perpendicular to the exterior front and rear walls of the crosshead. While this prior art crosshead design is intuitively simple and well-adapted to its present uses and purposes, this results in a very heavy and expensive crosshead. Additionally, crossheads of the prior art may include offset cast portions for the apertures for receiving the columns of the universal testing machine. This, in particular, requires a large special shape casting to obtain the correct shape to work with a universal test machine. Purchasing a casting requires high upfront fees in the form of pattern charges and storage of the pattern. Additionally, castings of this size are more expensive than a purchased steel plate stock in the typical volumes employed.

OBJECTS AND SUMMARY OF THE INVENTION

It is therefore an object of the present invention to provide a crosshead for a universal testing machine which can be produced at reduced cost.

It is therefore a further object of the present invention to provide a crosshead for a universal testing machine which achieves the above object without requiring any substantial or costly modifications in the universal testing machine.

These and other objects are attained by providing a rectangular crosshead design with a wedge pocket machined at an angle instead of perpendicular to the front surface of the crosshead. This allows a rectangular steel plate to be oriented to match the column locations of the universal testing machine so that no little or no modifications to the universal testing machine are required. Due to the rectangular shape, the material cost is significantly reduced as no special casting shape is required. Steel plate stock can be used thereby eliminating the pattern and pattern storage fees. This can result in as much as a thirty percent or more savings in many applications.

DESCRIPTION OF THE DRAWINGS

Further objects and advantages of the invention will become apparent from the following description and claims, and from the accompanying drawings, wherein:

DETAILED DESCRIPTION OF THE PREFERRED EMBODIMENT

Figure 1:
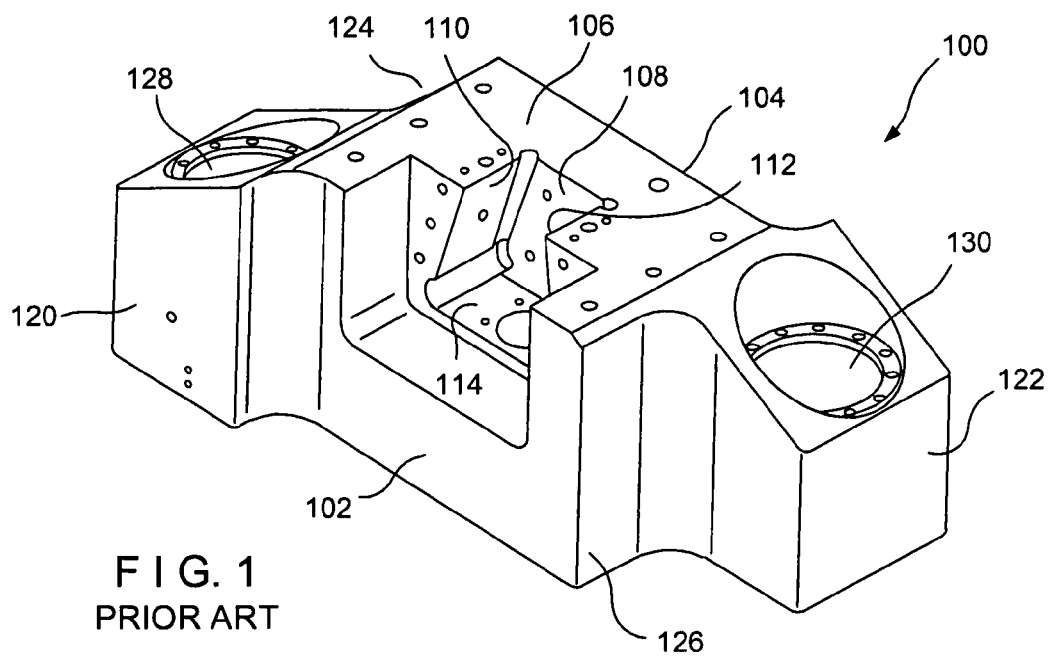
FIG. 1 is a front perspective view of a prior art crosshead with offset column locations.
Figure 2:
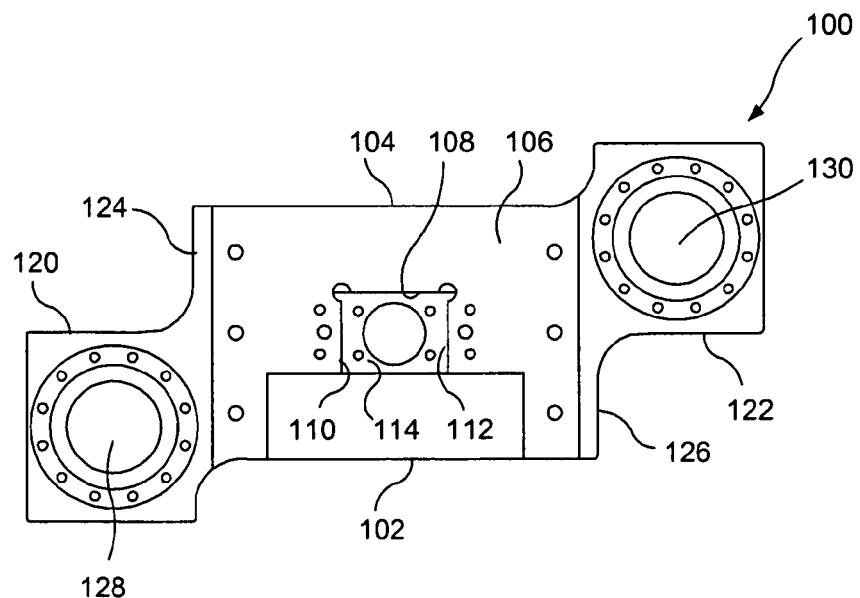
FIG. 2 is a top plan view of a prior art crosshead with offset column locations.

Referring now to the drawings in detail wherein like numerals indicate like elements throughout the several views, one sees that FIGS. 1 and 2 illustrate a prior art crosshead 100 which is formed by casting. Prior art crosshead 100 includes a front wall 102 and a rear wall 104 bounding the central portion 106. Wedge pocket 108 with inclined side walls 110, 112 and bottom wall 114 is formed within central portion 106. Inclined side walls 110, 112 and bottom wall 114 are all formed to be perpendicular with front and rear walls 102, 104.

The configuration of the inclined sidewalls 110, 112 within wedge pocket 108 allows jaws (not shown) to be inserted into wedge pocket 108 and a tensile (or similar) testing specimen (not shown) to be placed between the jaws or within a jaw assembly. Thereafter, during tensile or similar on the specimen, the jaws or jaw assembly are urged upwardly into a progressively narrowing gap between the inclined sidewalls 110, 112, the jaws or jaw assembly are urged into a progressively tighter grip on the specimen.

First and second offset cast portions 120, 122 are formed in mutually offset positions on respective first and second sides 124, 126 of crosshead 100. First and second offset cast portions 120, 122 include respective first and second column apertures 128, 130 for receiving the threaded columns of the universal testing machine. The interior of first and second column apertures 128, 130 typically include threaded nut assemblies.

Due to the intricate shape of the prior art crosshead 100, special casting is required which, as described above, is relatively expensive.

Figure 3:
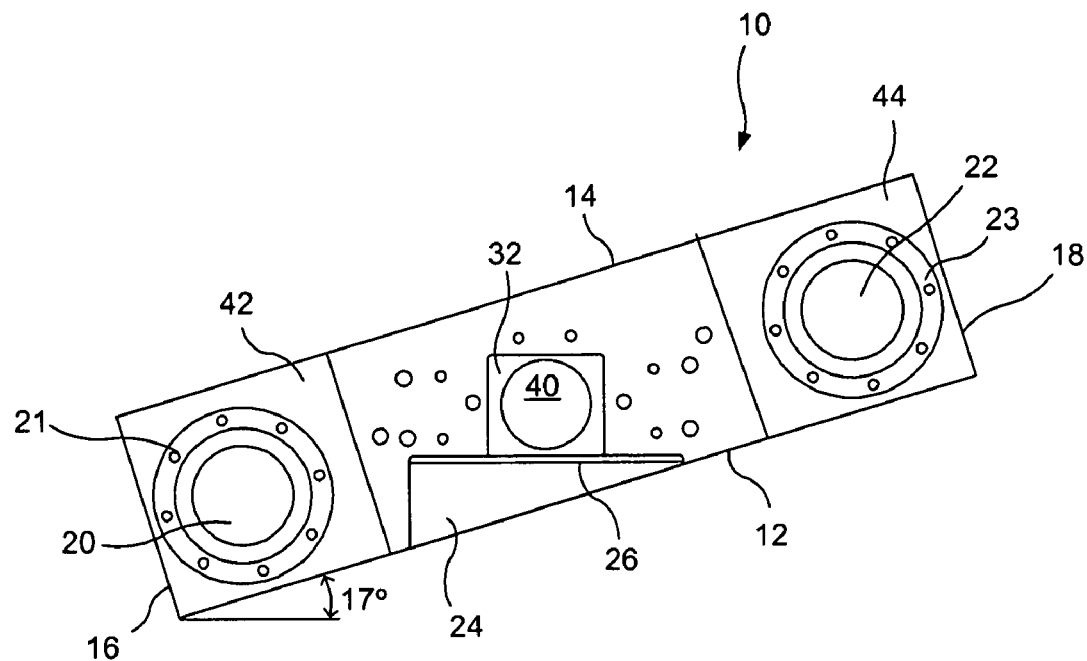
FIG. 3 is a top plan view of the crosshead design of the present invention.
Figure 4:
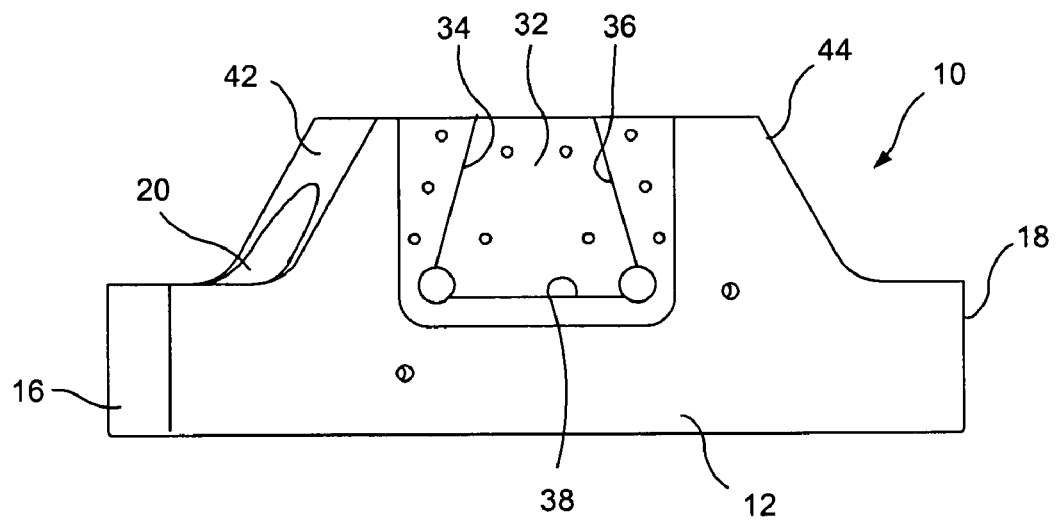
FIG. 4 is a front plan view of the crosshead design of the present invention, shown at a similar angle as illustrated in FIG. 3.
Figure 5:
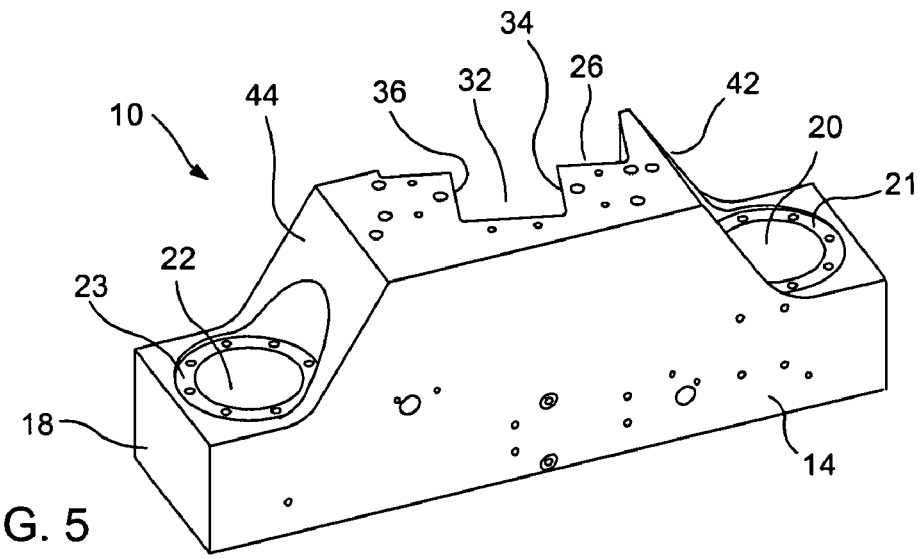
FIG. 5 is a rear perspective view of the crosshead design of the present invention.
Figure 6:
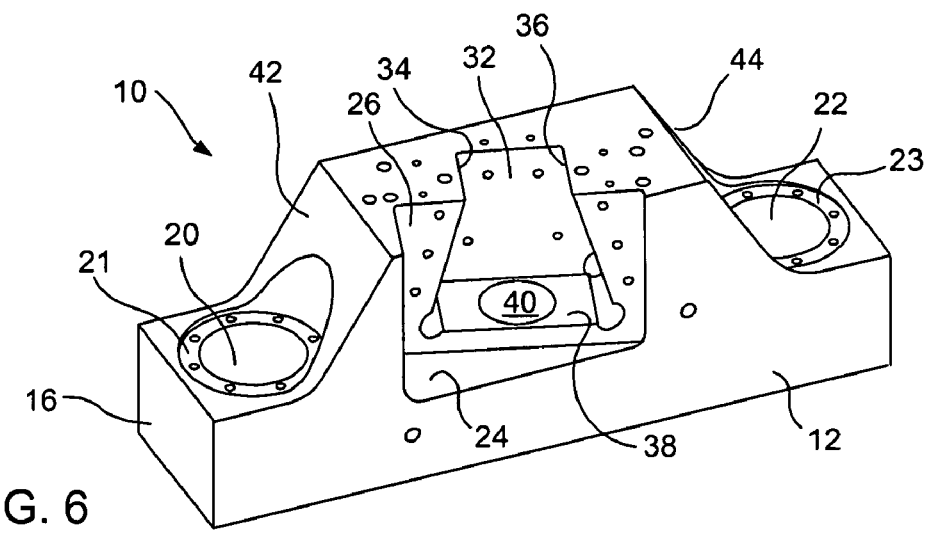
FIG. 6 is a front perspective view of the crosshead design of the present invention.

FIGS. 3-9 illustrate various views of crosshead 10, an embodiment of the present invention. Crosshead 10 is typically formed from rectangular torch cut plate stock rather than by casting. When viewed from above, as shown in FIG. 3, has a rectangular cross section with front face 12, rear face 14, left end face 16 and right end face 18. First and second column apertures 20, 22 are formed inwardly adjacent from respective left and right faces 16, 18 and are configured and arranged to receive the threaded columns (see elements 504, 506 of FIG. 10) of the universal testing machine (see element 500 of FIG. 10). First and second column apertures 20, 22 include threaded nut assemblies 21, 23 through which the threaded columns of the universal test machine pass, and which are intended to operate substantially the same as those in the prior art.

Triangular wedge 24 is excised or otherwise formed so as to create interior face 26 which is typically oriented about 17° (rather than 0°) with respect to front face 12, and therefore 73° (rather than 90°) with respect to the left and right faces 16, 18. This angle may vary somewhat (depending upon the degree of relative offset of the cast portions 120, 122 in the prior art crosshead 100 of FIGS. 1 and 2 which is to be replaced by the crosshead 10 of FIGS. 3-9), but interior face 26 is envisioned typically to be something other than parallel or perpendicular with respect to front face 12 or with respect to an imaginary line drawn between the centers or axes of first and second column apertures 20, 22. Wedge pocket 32 is formed with internal walls perpendicular to interior face 26. More specifically, inclined internal side walls 34, 36 and bottom internal wall 38 are all formed to be perpendicular with face 26 and hence not perpendicular with front and rear faces 12, 14.

Figure 7:
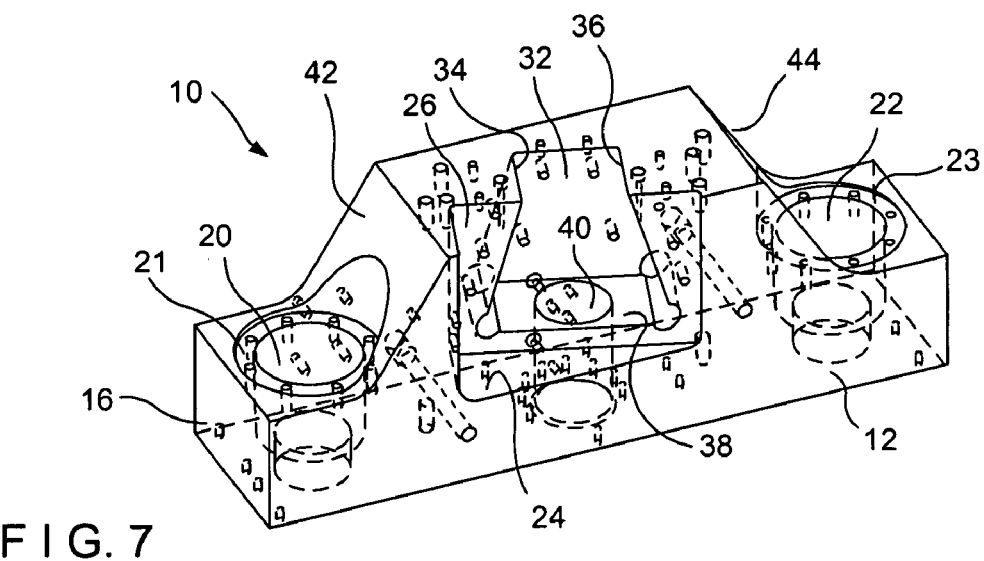
FIG. 7 is a front perspective view, partially in phantom, of the crosshead design of the present invention.

As shown in FIG. 7, passageway 40 extends from bottom internal wall 38 through the base of crosshead 10 thereby encompassing piston 78 which rises to urge the jaws 52, 54 into a tightened position around the specimen (not shown).

Figure 8:
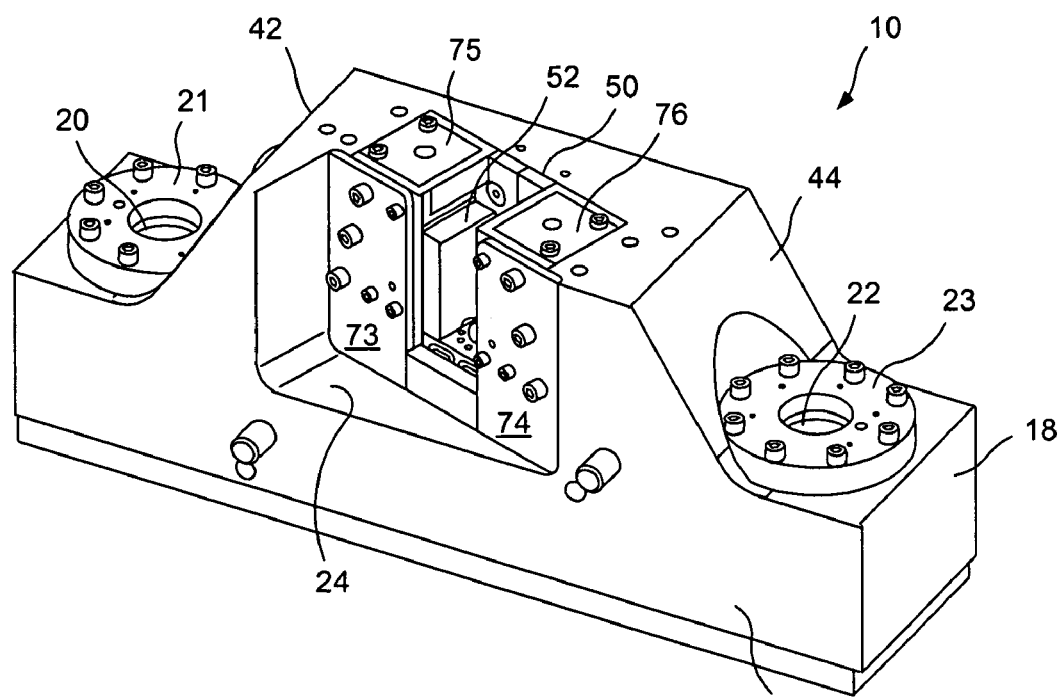
FIG. 8 is a front perspective view of the crosshead design of the present invention, illustrating the jaws and associated mounting components.
Figure 9:
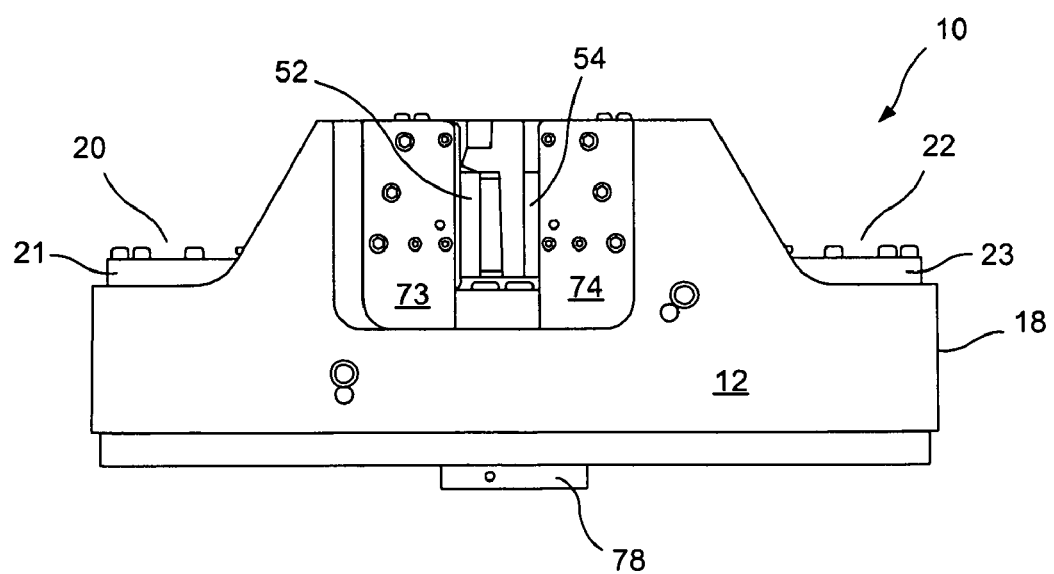
FIG. 9 is a front plan view of the crosshead design of the present invention, illustrating the jaws and associated mounting components.

As shown in FIGS. 8 and 9, typically jaw assembly 50 is formed from jaws 52, 54 with respective outer inclined walls (not shown) complementary to the inclined internal sidewalls 34, 36. Left and right front support plates 73, 74 hold the jaw assembly 50 in place, with debris covers 75, 76 positioned thereover.

As shown in FIGS. 4-9, material is excised or otherwise removed (or not initially formed) from the upper portions inwardly adjacent from left and right faces 16, 18, generally in the area of first and second column apertures 20, 22 to create areas of reduced height 42, 44.

The resulting configuration allows the crosshead 10 to be formed from torch cut plate stock rather than the casting of the prior art, thereby resulting in substantially reduced weight and manufacturing costs. Additionally, the relative orientations of the first and second column apertures 20, 22 and the wedge pocket 32 are maintained so as to be substantially identical to the corresponding elements of the prior art crosshead 100 of FIGS. 1 and 2, thereby allowing the prior art crosshead 100 to be replaced by crosshead 10 without substantial modification to the universal testing machine 500 of FIG. 10.

Figure 10:
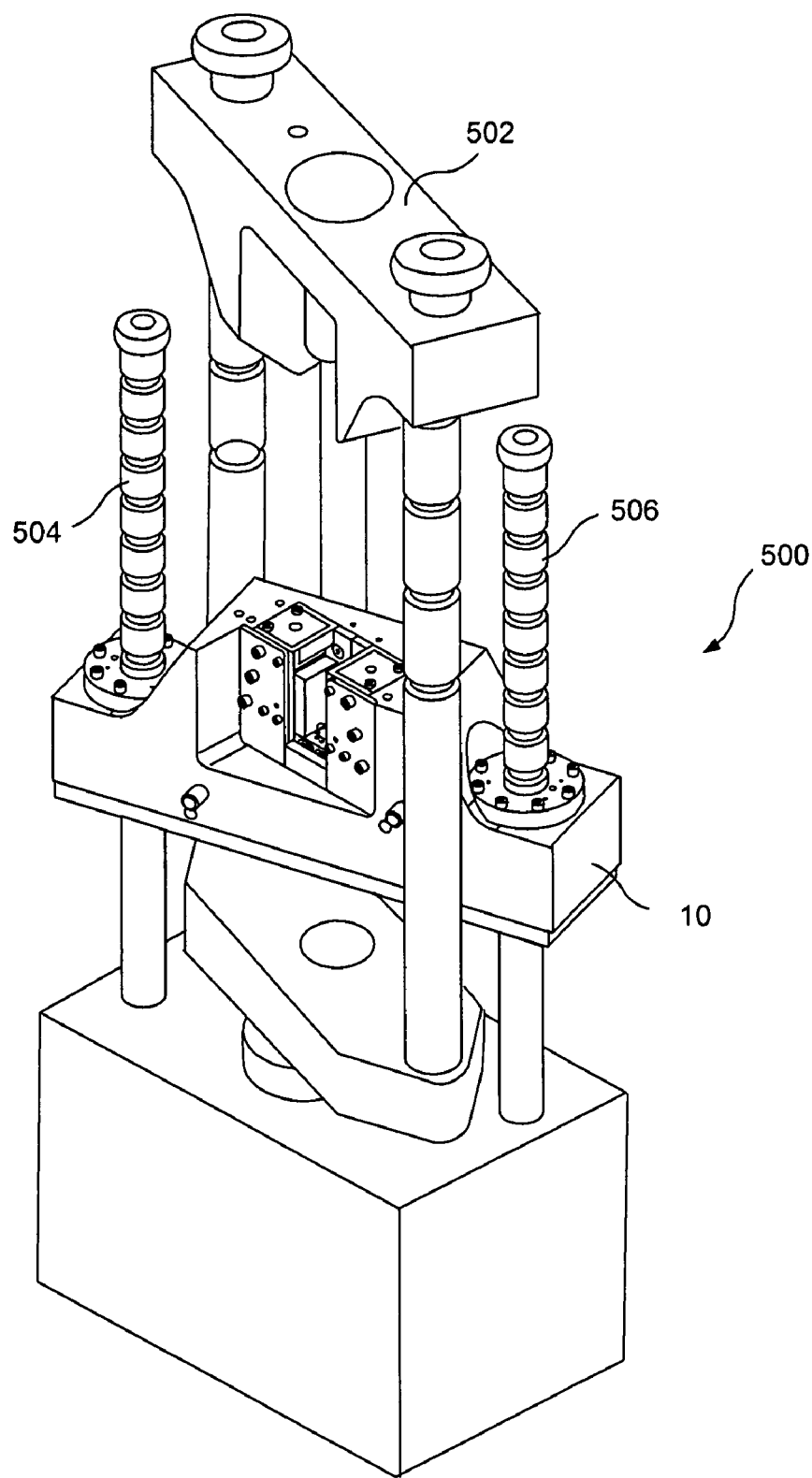
FIG. 10 is a perspective view of a universal testing machine configured to utilize the crosshead design of the present invention.

Crosshead 10 is used in the universal testing machine 500 as shown in FIG. 10. The sample or specimen (not shown) is engaged by the jaws of the fixed cross portion 502 and by the jaws of crosshead 10. The threaded columns 504, 506 pass through threaded nut assemblies 21, 23, and tensile or similar testing is performed in a manner with the universal testing machine 500 functioning in a conventional manner.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A crosshead for a testing apparatus, including:
   a front face, a rear face, and side faces;
   a top face extending between said front and rear faces;
   a wedge shaped pocket formed between said front face and said rear face, said wedge shaped pocket being formed from internal walls inclined with respect to said top face; and
   wherein said internal walls are formed at angles other than 0 or 90 degrees with respect to said front and rear faces and with respect to said side faces.

2. The crosshead of claim 1 wherein said front face is parallel to said rear face.

3. The crosshead of claim 2 wherein an interior face is formed perpendicularly to said internal walls.

4. A crosshead for a testing apparatus, including:
   a front face and a rear face, said front face being parallel to said rear face;
   a wedge shaped pocket formed between said front face and said rear face, said wedge shaped pocket being formed from internal walls;
   an interior face formed at an angle other than 0 or 90 degrees with respect to said front and rear faces; and
   wherein said internal walls of the wedge shaped pocket are formed perpendicularly with respect to said interior face.

5. The crosshead of claim 4 wherein said internal walls include a bottom wall and first and second inclined walls.

6. The crosshead of claim 5 wherein said first and second inclined walls are configured and arranged to receive a pair of jaws for engaging a specimen, and wherein gripping force exerted by the pair of jaws increases as tensile force on the specimen increases.

7. The crosshead of claim 6 includes a piston which can move through an aperture in said bottom wall, thereby extending into said wedge shaped pocket.

8. The crosshead of claim 7 wherein the crosshead is formed of torch cut plate stock.

9. The crosshead of claim 8 wherein said angle is substantially 17 degrees.

10. A crosshead for a testing apparatus, including:
    a rectangular cross section, including a front face, a rear face parallel to said front face, a first end face and a second end face;
    a wedge shaped pocket formed between said front face and said rear face, said wedge shaped pocket being formed from internal walls;
    an interior face, wherein said internal walls of the wedge shaped pocket are formed perpendicularly with respect to the interior face;
    a first threaded aperture and a second threaded aperture formed inwardly adjacent from said first end face and said second end face, respectively, for receiving threaded columns of a testing apparatus; and
    wherein at least one of said internal walls is formed at an angle other than 0 or 90 degrees with respect to said front and rear faces.

11. The crosshead of claim 10 wherein said interior walls include a bottom wall and first and second inclined walls.

12. The crosshead of claim 11 wherein said first and second inclined walls are configured and arranged to receive a pair of jaws for engaging a specimen, and wherein gripping force exerted by the pair of jaws increases as tensile force on the specimen increases.

13. The crosshead of claim 12 includes a piston which can move through an aperture in said bottom wall, thereby extending into said wedge shaped pocket.

14. The crosshead of claim 13 wherein the crosshead is formed of torch cut plate stock.

15. The crosshead of claim 14 wherein said angle is substantially 73 degrees.

* * * * *